OR 4,005,926

United States

Neale et al.

[11] B 4,005,926
[45] Feb. 1, 1977

[54] SCANNING DEVICE

[75] Inventors: Denis Manktelow Neale; Michael Gordon Throssell, both of Ilford, England

[73] Assignee: Ilford Limited, Ilford, England

[22] Filed: May 10, 1974

[21] Appl. No.: 469,036

[44] Published under the second Trial Voluntary Protest Program on March 16, 1976 as document No. B 469,036.

[30] Foreign Application Priority Data

May 16, 1973 United Kingdom ............ 23349/73

[52] U.S. Cl. .................................. 350/7; 356/158; 356/200; 356/203
[51] Int. Cl.² .......................................... G02B 27/17
[58] Field of Search ............... 350/7, 285; 356/158, 356/199, 200, 203; 178/7.6

[56] References Cited

UNITED STATES PATENTS

| | | | |
|---|---|---|---|
| 3,206,606 | 9/1965 | Burgo et al. | 356/200 |
| 3,485,546 | 12/1969 | Roth | 178/7.6 |
| 3,556,664 | 1/1971 | Blaisdell et al. | 356/200 |
| 3,573,849 | 4/1971 | Herriot et al. | 350/7 |
| 3,574,469 | 4/1971 | Emerson | 356/200 |
| 3,646,568 | 2/1972 | Woywood | 350/7 |
| 3,693,021 | 9/1972 | Lake, Jr. et al. | 356/200 |

*Primary Examiner*—Alfred E. Smith
*Assistant Examiner*—Richard A. Rosenberger
*Attorney, Agent, or Firm*—Wenderoth, Lind & Ponack

[57] ABSTRACT

A method of scanning a path on a surface by means of parallel beams of radiant energy whereby to scan at least one path across at least one surface which comprises directing at least two parallel beams of radiant energy to strike individually a like number of faces of a rotating mirror polygon as there are beams of radiant energy thereby deflecting the reflected paths of the said beams through angles equal to twice the angular subtense of each polygon face at the polygon center, the said parallel beams of radiant energy after reflection from the faces of the mirror polygon falling at least on one surface.

17 Claims, 4 Drawing Figures

SCANNING DEVICE

BACKGROUND OF THE INVENTION

This invention relates to scanning of surfaces in order to locate faults on the surfaces.

In a number of such scanning methods a beam of radiant energy is deflected by a rotating mirror polygon on to the surface to be scanned. The angle at which the beam strikes the surface can be chosen to suit the differing requirements of scanning systems in which the surfaces are inspected by reflection or by transmission. The amount of radiant energy reflected or transmitted by the surface is monitored by electronic means, for example a photocell, and any change noted, such changes indicating faults on the surface being scanned. Examples of surfaces which can be scanned are webs of film material and in particular coated webs of photographic film material.

SUMMARY OF THE INVENTION

The object of the present invention is to provide a method of scanning surfaces which makes multiple use of a rotating mirror polygon which polygon is an expensive item in the scanning apparatus.

According to the present invention there is provided a method of scanning a path on a surface by means of parallel beams of radiant energy whereby to scan at least one path across at least one surface which comprises directing at least two parallel beams of radiant energy to strike individually a like number of faces of a rotating mirror polygon as there are beams of radiant energy thereby deflecting the reflected paths of the beams through angles equal to twice the angular subtense of each polygon face at the polygon centre, the parallel beams of radiant energy after reflection from the faces of the mirror polygon falling at least on one surface.

Preferably only two substantially parallel beams of radiant energy are employed.

In the preferred method of the present invention the two substantially parallel beams of radiant energy are produced from a single source. Examples of single sources of radiant energy are tungsten filament lamps. These lamps may produce visible light or infra red radiant energy, this latter being of particular use when visible light sensitive coatings on film or paper material are being scanned. Other suitable single sources of radiant energy are gas discharge lamps and lasers.

By means of the method of the present invention it is possible to produce, by incorporating suitable optical means, first and second beams of different cross-sectional area. For example if two beams are produced one may have the cross-sectional shape of a slit and other of a spot. When such beams are used to scan the same surface the "slit" beam is used to locate longitudinal faults on the surface and the "spot" beam is used to locate discrete faults on the surface.

Preferably the reflected beams fall on a common surface. In this embodiment of the method of the invention the reflected beams may scan the same path on the common surface or the reflected beams may scan different paths on the common surface.

When the same path is scanned the beams are preferably of different cross-sections as just mentioned; the beams of different cross-section being used to locate different types of faults on the said common surface.

In the method of the present invention, and in particular in methods wherein two beams are employed, the two reflected beams may fall on the common surface simultaneously or they may fall on the common surface alternately. If the reflected beams are used to scan a common surface alternately, they may with advantage be derived from a single beam by use of a rotating mirror shutter located in the path of the beam before the beam strikes the mirror polygon.

In the method of the present invention when the reflected beams fall on a common surface they may fall on the common surface at different angles of incidence. In this case one beam may be used to scan the common surface by reflection and the other by transmission.

The method of the present invention, wherein the two reflected beams fall on the common surface alternately, finds great use in scanning travelling narrow webs of materials. In this case the paths which the two beams scan across the web surface follow sequentially in close proximity so that as the mirror polygon rotates one scan finishes on one side of the web as the next scan is starting on the other side of the web.

Using a single beam of finite width the scan can only take place while the whole of the beam is falling on one facet. If the effective beam width is half of the mirror size, this means that scanning of the web can only take place for half of the time because the other half of the time the beam is overlapping the edge of a mirror. With suitable choice of geometry, the double beam system of the present invention overcomes this by ensuring that one beam is always scanning the web while the other beam is changing to the next mirror. Since the scanning spot size is usually decided by faults resolution considerations and the web speed is fixed, a certain number of scans must take place per unit time for every part of the web to be covered. Because there is no lost time between scans, the rate of movement of the spot across the web may be approximately halved and the bandwidth of the detector system may also be halved with the attendant advantages of lower noise and a less critical choice of components.

In another embodiment of the present invention, and in particular in the preferred embodiment, wherein two beams are reflected from the rotating mirror polygon, one beam falls on a first surface and the second beam falls on a second surface. In this embodiment it is preferred that the instantaneous deflection of the first beam is through an equal angle to the instantaneous deflection of the second beam and in the same sense. In this embodiment of the present invention one single rotating mirrorpolygon may be used to scan two surfaces simultaneously, for example one travelling web of material may be located above the rotating mirror polygon and the other below the rotating mirror polygon.

The method of the present invention finds particular use in the scanning of the coated film material wherein various types of faults may be present. For example some of the faults can only be detected by reflection of the scanning beam from the surface of the film material and others can only be detected by transmission of the reflected beam through the web. When a panchromatic photographic web material is being scanned it is preferred that the energy source is of the infra-red producing type.

The invention will be described with reference to its use in the scanning of a travelling web of photographic material.

DETAILED DESCRIPTION OF THE INVENTION

Figure 1:
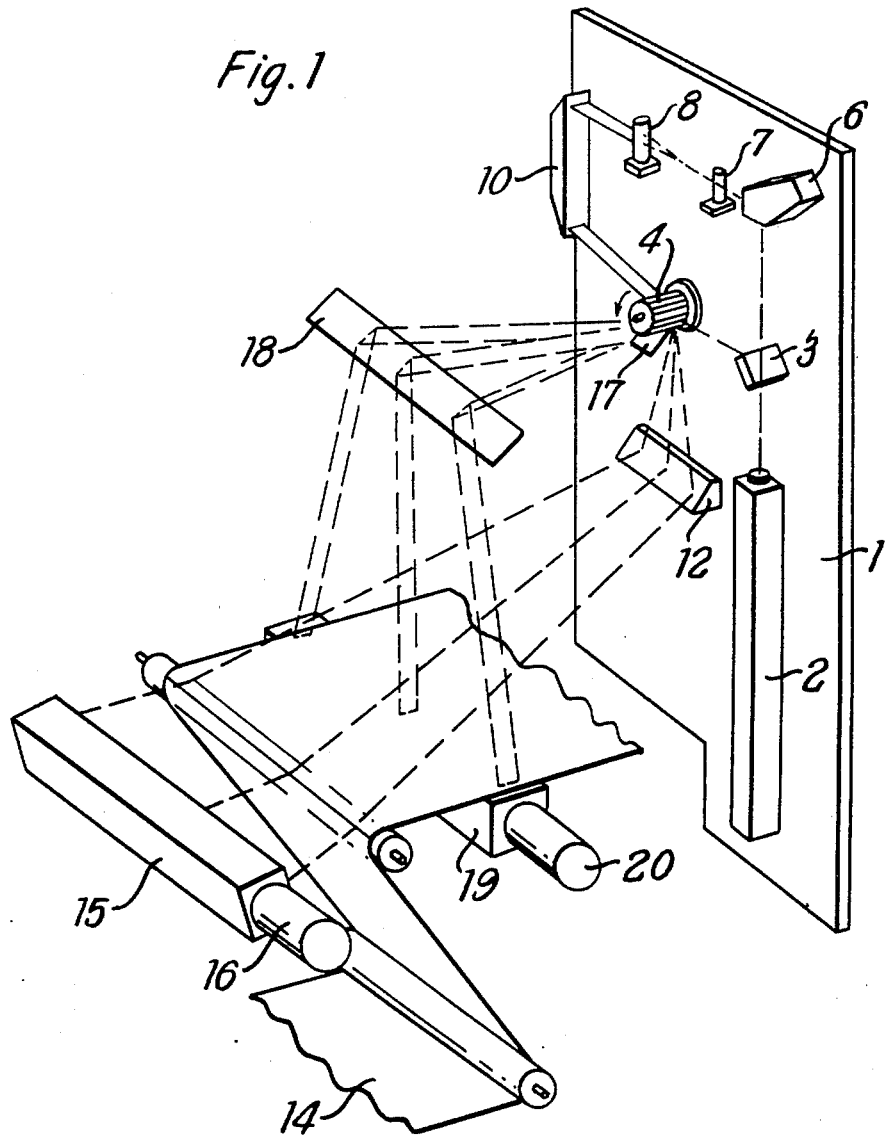
FIG. 1 is a perspective view of a scanning apparatus wherein two laser beams are reflected from the same rotating mirror polygon on to a travelling web of film material, one beam is reflected from the surface of the web and the other beam scans the surface by transmission.

In the FIG. 1 there is mounted on a backboard 1 a laser 2. Located above the laser 2 is a beam splitter 3. One beam of light is shown being reflected by the beam splitter 3 on to a rotating mirror polygon 4 which has twelve faces. The other beam of light is shown passing through the beam splitter 3, through a silvered pentagonal prism 6 and through two cylindrical lenses 7 and 8 which are used to produce a flat cross-sectional beam. The flat cross-sectional beam then passes through a silvered prism 10 and is reflected on to another face of the rotating mirror polygon 4.

The beam of light which was reflected by the beam splitter 3 after striking one face of the mirror polygon 4 is deflected on to a plane mirror 12 which is at an angle of 50° to the horizontal. This mirror deflects the laser beam at an oblique angle on to a travelling web of film material 14 which is located below the back board 1 on which the first listed components of the apparatus are located.

The laser beam which is deflected by the plane mirror 12 on to the film web 14 strikes the film web at such an angle that the beam is reflected from the surface of the film web 14. After reflection from the surface of the film web 14 the laser beam is collected by a collector 15, at one end of which is located a photocell device 16.

The other laser beam which is reflected on to the mirror polygon 4 by the silvered prism 10 is then deflected by the mirror polygon 4 on to a plane mirror 17 located at 45° beneath the polygon 4 and from thence to a further plane mirror 18 which is located at an angle of 45° above the path of the film web 14. This laser beam after reflection from the mirror 18 scans a path across the film web. The laser beam strikes the film web normal to the path of the film web and part of the energy of the laser beam is transmitted through the film web and is collected in the transmission collector 19 which has a photocell means 20 at one end thereof.

By use of the method of the present invention as just described two laser beams simultaneously scan the same travelling film web using one only one rotating mirror polygon. One laser beam is a slit beam which is used to locate faults by transmission and the other beam is a spot beam which is used to locate discrete faults on the film web surface by reflection from the web surface.

If it is required that the two laser beams shall scan the same travelling film web alternately, the beam splitter 3 may be replaced by a sectored mirror shutter rotated in synchronism with the polygon. By this means, substantially all the energy of the laser 2 can alternately be allowed to follow the path leading to mirror 12 or be diverted to follow the path leading to mirror 17.

Figure 2:
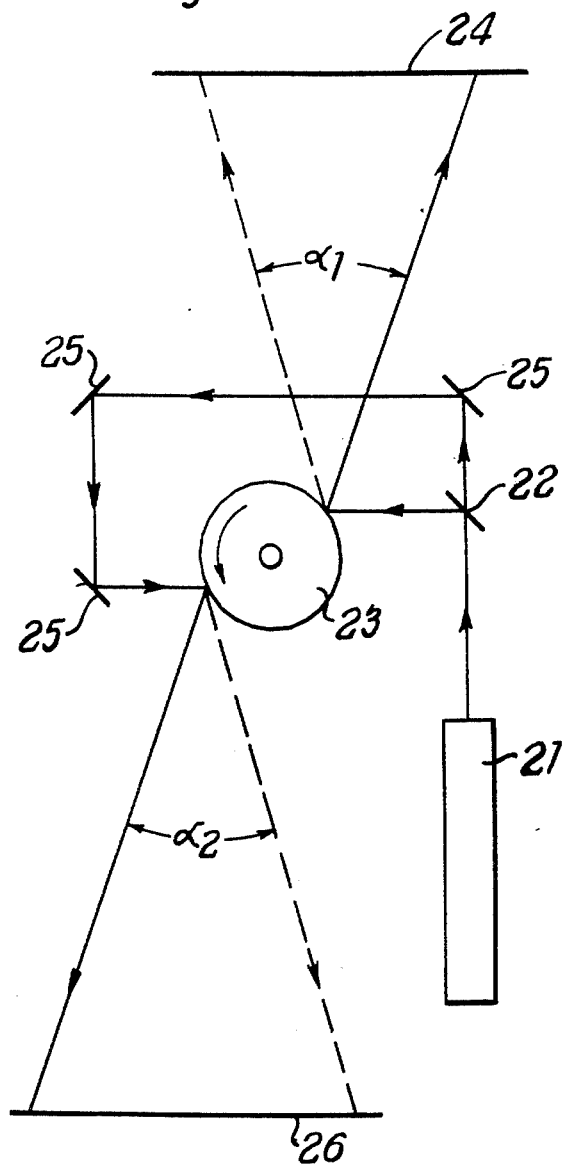
FIG. 2 shows in diagrammatic form the method of scanning wherein of two beams reflected from the same polygon, one beam falls on a first surface and the other beam falls on a second surface.

In FIG. 2 a laser 21 produces a beam of light which is directed to a beam splitter 22 which divides the light equally. One half of the light (the first beam) is reflected by the beam splitter 22 on to a rotating mirror polygon 23 and from thence it is caused to scan a first travelling web 24. The other half of the light (the second beam) which is transmitted by the beam splitter 22 is reflected through three reflecting mirrors 25 by 270° so that it strikes the polygon 23 diametrically opposite the point at which the first beam strikes the polygon. The second beam of light is caused to scan a second travelling web 25 by the rotating polygon 23.

The instantaneous deflection of the first beam from the polygon 23 is through an equal angle to the instantaneous deflection of the second beam from the polygon and in the same sense, that is to say $\alpha_1$ equals $\alpha_2$.

Thus in the method shown in FIG. 2 two travelling film webs may simultaneously be scanned using only one laser and one rotating polygon.

Figure 3:
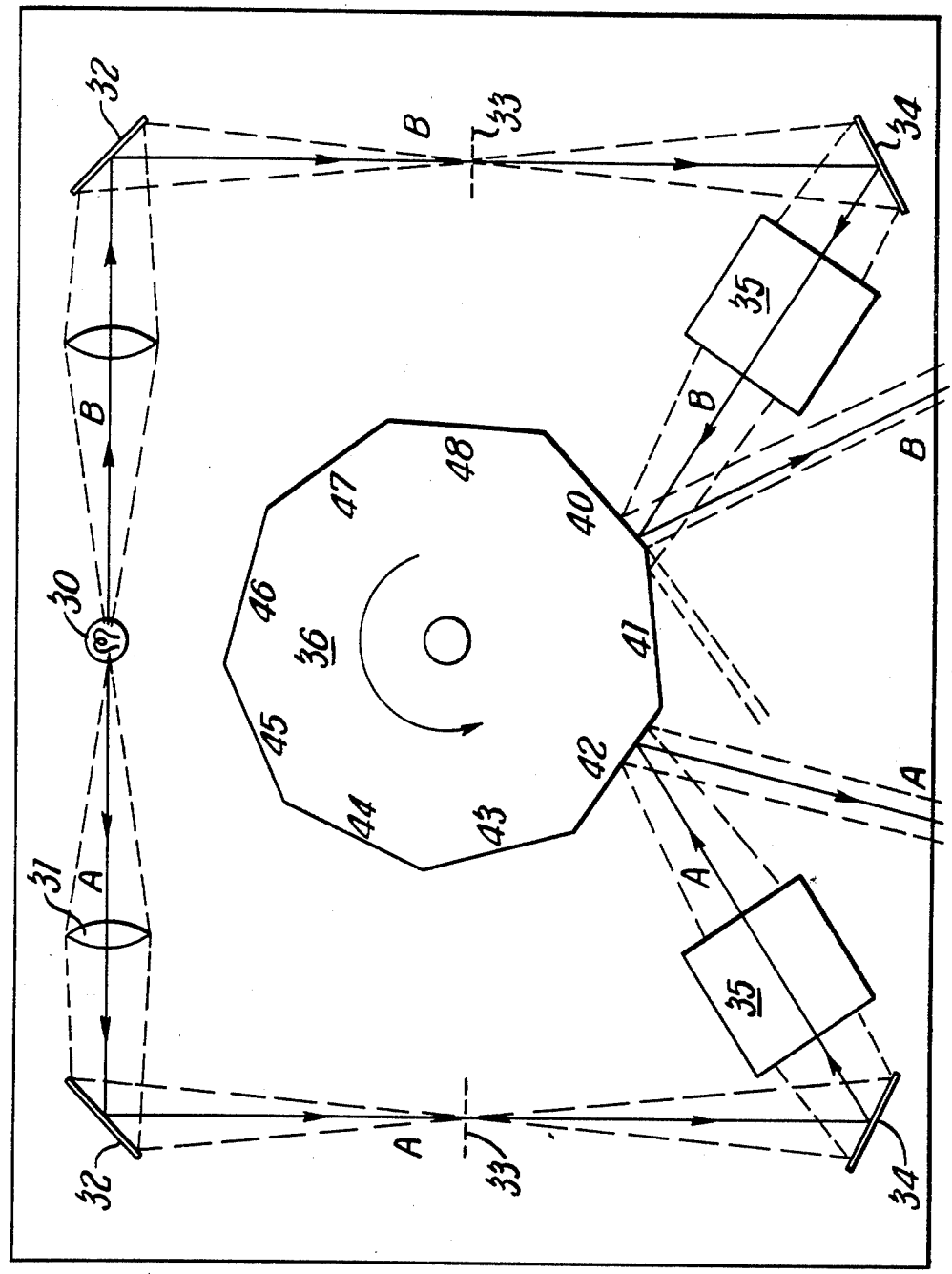
FIG. 3 shows the method of scanning wherein two beams reflected from the same polygon fall on a common surface alternatively.

In FIG. 3 two beams of light A and B are produced from a tungsten filament lamp 30. Beams A and B follow similar paths and both pass through a condenser lens 31 and then they are reflected through 90° by a totally reflecting mirror 32. They then pass through a mask 33 and are reflected through an angle by a totally reflecting mirror 34 through a projection lens 35. Both the beams A and B fall continuously on a rotating mirror polygon 36.

The shape of the mask determines the shape of the scanning beams A and B as the image of the mask 33 is focussed by the objective lens 35 on the the surface of the web after reflection from the rotating mirror polygon 36. The polygon 36 has 9 mirror faces 40–48.

Figure 4:
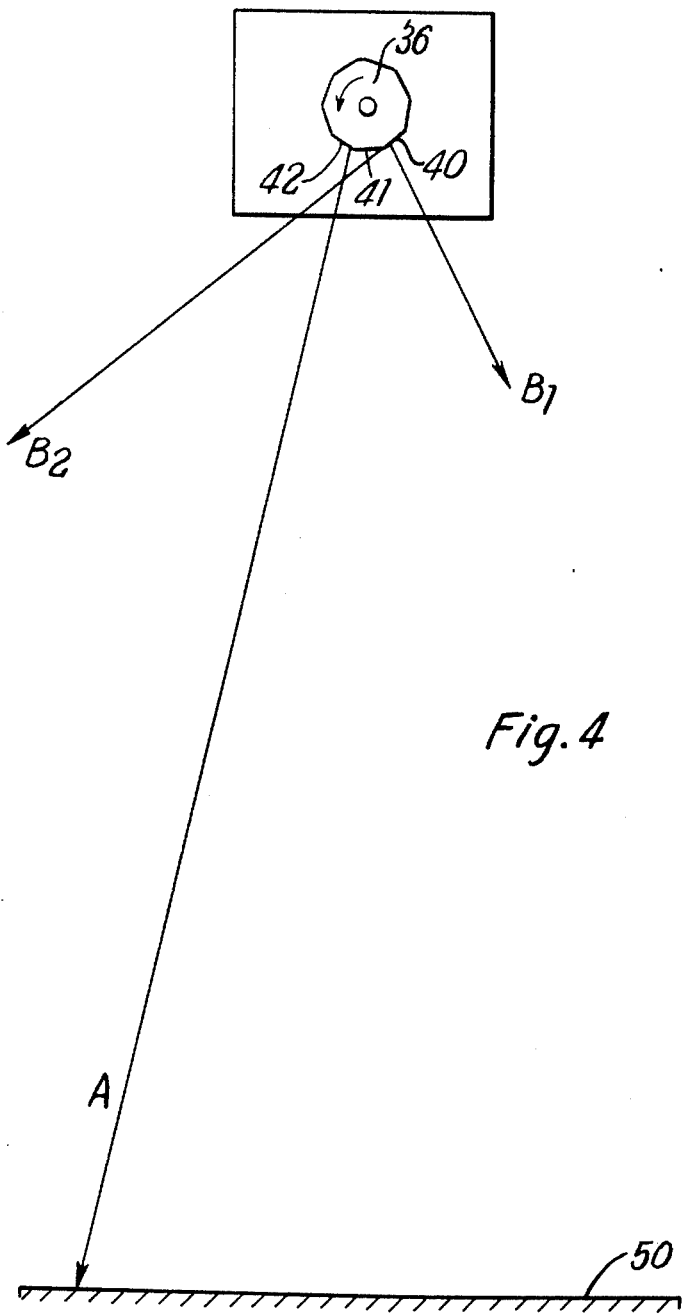
FIG. 4 shows in diagrammatic form the path of the beams of light employed in the method of FIG. 3.

The beams of light A and B are reflected by the rotating polygon as shown in FIG. 4.

In FIG. 4 the scanning beam A shown in FIG. 3 is being reflected from mirror 42 on to a travelling film web 50 and is just beginning its scan. Thus while beam A is being reflected from mirror 42 it will scan across the web 50. The scanning beam $B_1$ which is reflected from the mirror 40 has just completed its scan across the film web 50. Scanning beam $B_2$ which is light reflected from mirror 41 is the next scanning beam which will scan across the web 50 when beam A has completed its scan.

Thus in FIGS. 3 and 4 is shown the method wherein reflected beams fall on a common surface alternately. In this case film web 50 is comparatively narrow and the paths of the two beams of light A and B scan across the web surface sequentially in close proximity so that as the mirror polygon 36 rotates one scan finishes on one side of the web as the next scan is starting on the other side of the web. Thus scanning is not interrupted while the beams of light change from one mirror to the next as would happen if only one beam of light were used.

What we claim is:

1. A method of scanning surface areas, said method comprising:
   providing two substantially parallel beams of radiant energy of different cross-sectional area;
   directing said two beams to strike individually a like number of different faces of a rotating mirror polygon, thereby deflecting the reflected paths of said beams through angles equal to twice the angular subtense of each polygon face at the polygon center; and directing said two parallel beams of radiant energy after reflection from said faces of said mirror polygon onto at least one surface, thereby scanning with both said beams at least one path across said at least one surface.

2. A method according to claim 1, wherein said two beams of radiant energy are produced from the same source.

3. A method according to claim 2, wherein said source of radiant energy is a tungsten filament lamp.

4. A method according to claim 2, wherein said source of radiant energy is a gas discharge lamp.

5. A method according to claim 2, wherein said source of radiant energy is a laser.

6. A method according to claim 1, comprising directing both of the reflected radiant energy beams onto a common surface.

7. A method according to claim 6, comprising directing said two reflected radiant energy beams onto said common surface simultaneously.

8. A method accordng to claim 7, comprising directing said two beams of radiant energy onto said common surface at different angles of incidence.

9. A method according to claim 8, wherein one beam is used to scan a web by reflection and the other by transmission.

10. A method according to claim 7, wherein said common surface is a travelling web.

11. A method according to claim 10, wherein said web of material is a web of photographic material, and said radiant energy is infra-red radiation.

12. A method according to claim 6, comprising directing said two reflected radiant energy beams onto said common surface alternately.

13. A method according to claim 12, wherein said common surface is a travelling narrow web of material, and the paths which said two beams scan across said web surface follow sequentially in close proximity so that as said mirror polygon rotates one scan finishes on one side of said web as the next scan is starting on the other side of said web.

14. A method according to claim 1, comprising directing a first of said beams of radiant energy onto a first surface and directing a second of said beams of radiant energy onto a second surface.

15. A method according to claim 14, wherein the instantaneous deflection of the said first beam is through an equal angle to the instantaneous deflection of the said second beam and in the same sense.

16. A method according to claim 14, wherein said two surfaces onto which said two beams of radiant energy are directed are two travelling webs of material.

17. A method according to claim 1, comprising providing said rotating mirror polygon with a longitudinal axis and each of said faces being in a plane parallel with said axis.

* * * * *